(12) United States Patent
Najafi et al.

(10) Patent No.: US 10,820,809 B2
(45) Date of Patent: Nov. 3, 2020

(54) APPARATUS AND METHOD FOR DETECTING AND NOTIFYING POSTPARTUM HAEMORRHAGE

(71) Applicants: Tahereh Fathi Najafi, Mashhad (IR); Parsa Elyassirad, Birjand (IR)

(72) Inventors: Tahereh Fathi Najafi, Mashhad (IR); Parsa Elyassirad, Birjand (IR)

( * ) Notice: Subject to any disclaimer, the term of this patent is extended or adjusted under 35 U.S.C. 154(b) by 0 days.

(21) Appl. No.: 16/774,615

(22) Filed: Jan. 28, 2020

(65) Prior Publication Data

US 2020/0155016 A1    May 21, 2020

Related U.S. Application Data

(60) Provisional application No. 62/923,547, filed on Oct. 19, 2019.

(51) Int. Cl.

| | |
|---|---|
| *A61B 5/02* | (2006.01) |
| *A61M 27/00* | (2006.01) |
| *A61B 5/00* | (2006.01) |
| *A41B 9/04* | (2006.01) |
| *A61G 13/00* | (2006.01) |
| *A61G 13/10* | (2006.01) |
| *A61M 1/02* | (2006.01) |
| *A61J 1/10* | (2006.01) |

(52) U.S. Cl.
CPC ............ *A61B 5/02042* (2013.01); *A41B 9/04* (2013.01); *A61B 5/4343* (2013.01); *A61B 5/6804* (2013.01); *A61B 5/7405* (2013.01); *A61B 5/746* (2013.01); *A61G 13/0009* (2013.01); *A61G 13/102* (2013.01); *A61M 1/02* (2013.01); *A61M 27/00* (2013.01); *A41B 2400/22* (2013.01); *A61B 2505/05* (2013.01); *A61G 2203/44* (2013.01); *A61J 1/10* (2013.01); *A61M 2205/3393* (2013.01); *A61M 2210/14* (2013.01)

(58) Field of Classification Search
CPC .. A61B 5/4306; A61B 5/4343; A61B 5/02042
See application file for complete search history.

(56) References Cited

U.S. PATENT DOCUMENTS

2017/0185739 A1\* 6/2017 Gomez .................. G01G 19/44

\* cited by examiner

*Primary Examiner* — Puya Agahi
(74) *Attorney, Agent, or Firm* — Barry Choobin; Patent 360

(57) ABSTRACT

An apparatus for detecting and notifying occurrence of post-partum haemorrhage in female patients is envisaged. Continued tracking of the blood discharged from a female patient's body during labor as well as postnatal operation procedures is provided for, and as soon as the amount of blood discharged from the body of the female patient exceeds a predetermined threshold value, a light-based alarm and sound-based alarm are triggered. The apparatus includes a first connector connected to the female patient when she is on a Labor Recovery Delivery bed, and a second connector woven onto an undergarment to be worn by the female patient. The first connector and second connector are connected to single use, disposable blood collection bags, whose weights are measured using weight sensors for an accurate calculation of the total amount of the blood lost by the female patient during labor operation procedures and postnatal operation procedures.

8 Claims, 6 Drawing Sheets

APPARATUS AND METHOD FOR DETECTING AND NOTIFYING POSTPARTUM HAEMORRHAGE

BACKGROUND

Technical Field

The present disclosure relates to systems, apparatus, and methods that facilitate patient monitoring. Particularly, the present disclosure relates to systems, apparatus, and methods that monitor continued patient monitoring. More particularly, the present disclosure relates to systems, apparatus, and methods that facilitate an accurate measurement of the amount of blood loss during labor and postnatal operation procedures. The present disclosure also relates to systems, apparatus, and methods that automatically notify, in real-time and without manual intervention, to the clinical staff and caretakers, the occurrence of postpartum haemorrhage in a female patient.

Description of the Related Art

Worldwide, every year, more than half a million expectant mothers lose their lives while giving birth to a child, due to the complications arising from postpartum haemorrhage. Even today, despite all the advancements in the field of medicine and surgery, the complications arising out of postpartum haemorrhage during childbirth accounts for 'one' in 'six' lives every year in underdeveloped/developing countries, whereas in developed countries the ratio is 1:30,000, with only 'one' out of every thirty thousand expectant mothers being fatally affected every year. The aforementioned statistics unambiguously state the need for improved medical practices, both surgical and maternal, in underdeveloped and developing countries, and also the underlying phenomenon of high pregnancy related fatality rates in such underdeveloped and developing countries. Even though, postpartum haemorrhage and the complications arising therefrom have been regarded as one of the major contributors for maternal mortality, postpartum haemorrhage remains preventable, provided appropriate precautions, essentially surgical precautions, are undertaken in a timely manner, including providing the new mother with necessary medical care and supportive care.

Essentially, while providing supportive care to a new mother suffering from postpartum haemorrhage involves delivering blood directly into (a vein of) the new mother, providing medical care to a new mother (suffering from postpartum haemorrhage) involves performing uterine compression, dilation and curettage, balloon tamponade, and administering necessary hormones and uterotonic medications. However, it is absolutely necessary that the symptoms leading to postpartum haemorrhage, i.e., excessive loss of blood during labor-related operation procedures or postnatal operation procedures or both, are monitored in a timely manner and the healthcare personnel in charge of the well-being of an expecting mother or a new mother in the case of postnatal operation procedures, is automatically intimated, about the likely onset of postpartum haemorrhage in real-time and on an immediate basis. And therefore, it is advantageous to have a system (and a method) that continually monitors the amount of blood lost by a female patient during both the labor-related operation procedures and postpartum operation procedures, and notifies the concerned healthcare personnel (clinical staff, caretakers in charge of the well-being of female patient) in case excessive loss of blood is detected in the said female patient. It is also advantageous to have a system and a method that automatically generates an alarm, either a sound-based alarm or a light-based alarm or both, indicative of excessive loss of blood, without necessitating manual monitoring and intervention.

One of the major steps associated with early (or timely) detection of postpartum haemorrhage in a female patient involves determining the amount of blood soaked up by blood draw sheets during labor-related and postnatal operation procedures. And, typically, a mere laboratory measurement or a measurement performed solely via visual inspection is highly inadequate for accurately determining the total amount of blood lost by the female patient (during labor-related and postnatal operation procedures). And therefore, it is even more advantageous to have a system and a method that obviates manual inspections and manual interventions, and instead relies upon an accurate measurement of the amount of blood lost from the body of the female patient, to automatically generate a sound-based alarm as well as a light-based alarm, thereby alerting the concerned healthcare personnel to the occurrence of postpartum haemorrhage in the female patient, in a timely manner. It is also advantageous to have a system and a method that provides healthcare personnel with an accurate and real-time measurement of the total blood lost by the female patient across both the labor related operation procedures and postnatal operation procedures.

OBJECTS

An object of the present disclosure is to envisage a system and a method useable for collecting blood discharged from a female patient's body during labor operation procedures and postnatal operation procedures, and automatically detecting the onset of postpartum haemorrhage in a female patient.

Yet another object of the present disclosure is to envisage a system and a method that automatically generates a sound-based alarm and a light-based alarm, indicating the onset of postpartum haemorrhage in a female patient.

One more object of the present disclosure is to envisage a system and a method that obviates the need for manual interventions in detection of postpartum haemorrhage.

Still a further object of the present disclosure is to envisage a system and a method that obviates the need for blood draw sheets to be visually inspected for an assessment of the amount of blood discharged during labor and postnatal operation procedures, and instead provides an accurate measurement of the discharged blood, based on the weight of the bags holding the discharged blood.

Yet another object of the present disclosure is to envisage a system and method that provides an accurate measurement of the amount of blood lost during labor operation procedures as well as the amount of blood absorbed from the (body of the) female patient via the use of sanitary absorbents and sterile gases.

Another object of the present disclosure is to envisage easy-to-use, portable electronic measurement apparatus that accurately measures the quantum of the blood lost by a female patient during childbirth.

SUMMARY

The present disclosure envisages an apparatus and a method for detecting and notifying, essentially to the clinical staff, an occurrence of post-partum hemorrhage (PPH) in female patients. The apparatus and the method envisaged by the present disclosure provide for continual tracking of the blood discharged from the body of a female patient, both during the labor operation procedures and postnatal operation procedures/postnatal care procedures. And as soon as the amount of blood discharged from the body of the female patient exceeds a predetermined threshold value, the apparatus and the method trigger both a light-based alarm and sound-based alarm, either simultaneously or in a pre-designated order, which would entail both the alarms being triggered one after the other, with the time-gap between the two alarms set to a predetermined time period.

The Apparatus envisaged by the present disclosure involves two types of hospital beds. The first one being a Labor Delivery Recovery (LDR) bed used only during labor operation procedures and a type-9 bed used only during postnatal operation procedures. In accordance with the present disclosure, when the female patient is undergoing operation procedures relevant to the state of labor, she is typically accommodated on the LDR bed. The LDR bed, in accordance with the present disclosure, includes an opening created on the anterior side thereof, such that when the female patient is accommodated on the LDR bed, the female patient's posterior pelvic region coincides with and is accessible through the opening. Subsequently, a first connector, incorporating a substantially cone-shaped proximal end and an elongated, hose shaped distal end is passed through the opening, and the substantially cone-shaped proximal end is attached to the posterior pelvic region of the female patient, such that the said proximal end of the first connector is in skin-contact with the posterior pelvic region. Subsequently, the elongated, hose shaped distal end of the first connector is connected to a blood holding bag located in proximity to the LDR bed. And whenever there occurs a blood-discharge from the body of the female patient, the discharged blood flows through the proximal end and distal end of the first connector and gets collected in the blood holding bag. The blood holding bag and essentially the inner surface of the blood holding bag is coated with an anticoagulant such as Sodium Citrate to prevent coagulation of the collected blood. Essentially, the weight of the blood holding bag—indicative of the amount of blood discharged blood held therein—is measured using a first weight sensor. Essentially, the weight of the blood holding bag is directly proportional to and indicative of the amount of blood lost by the female patient during the labor operation procedures. Essentially, the first weight sensor is equipped with a Radio Frequency Transceiver (RF-Transceiver), which transmits the measured (sensed) weight of the blood holding bag, onto a microcontroller (processor) having processing capabilities. The microcontroller essentially stores the measured (sensed) weight of the blood holding bag on a flash memory device connected thereto via an electronic circuitry. Essentially, the first weight sensor is also connected to the microcontroller via the said electronic circuitry.

In accordance with the present disclosure, after the termination of the labor operation procedures and after the culmination of the labor operation procedures into childbirth, the female patient is shifted from the LDR bed to a type-9 bed specifically configured for postnatal/post-partum operation procedures and necessary care. In accordance with the present disclosure, the female patient is shifted onto a type-9 bed preconfigured with a hole in the middle thereof. The hole is preferably located at the lateral and longitudinal mid-point of the type-9 bed. Essentially, prior to being transferred onto the type-9 bed, the female patient is instructed to wear a specially configured undergarment, which includes a second connector woven into it. The second connector is woven onto the (specially configured) undergarment such that the second connector is in skin-contact with the posterior pelvic region of the female patient when she wears the undergarment. The second connector, in accordance with the present disclosure, facilitates measurement of the amount of blood absorbed from the female patient's body via the use of sanitary absorbents and sanitary gases.

Essentially, a substantially rectangular proximal end of the second connector is woven onto the undergarment and is held in skin-contact with the female patient wearing the undergarment, with an elongated, hose shaped distal end of the second connector is passed through the hole in the Type-9 bed and is connected to a blood transfusion bag located in proximity to the Type-9 bed. Essentially, the blood discharged from the female patient's body, i.e., the posterior pelvic region, during postnatal operation procedures/postnatal care procedures, flows through the proximal end of the second connector woven onto the female patient's undergarment, to the distal end of the second connector, and finally to the blood transfusion bag connected to the distal end of the second connector.

Essentially, the weight of the blood transfusion bag—indicative of the amount of discharged blood held therein—is measured using a second weight sensor. Essentially, the weight of the blood transfusion bag is directly proportional to and indicative of the amount of blood lost by the female patient during postnatal operation procedures/postnatal care procedures. Essentially, the second weight sensor is also equipped with a Radio Frequency Transceiver (RF-Transceiver), which transmits the measured (sensed) weight of the blood transfusion bag, onto the microcontroller. The microcontroller essentially stores the measured (sensed) weight of the blood transfusion bag on the flash memory device.

In accordance with the present disclosure, the microcontroller is communicably coupled to the first sensor, second sensor, sound-based alarm, light-based alarm, and a Liquid Crystal Display monitor, via the said electronic circuitry. Essentially, the sound-based alarm and the light-based alarm are positioned in such a way that they are always rendered visible and audible (respectively) to the clinical staff and the caretakers in charge of the well-being of the female patient. Essentially, the Liquid Crystal Display monitor is also positioned in such a way that it is always visible and accessible to the clinical staff and the caretakers.

The microcontroller essentially calculates the total amount of blood loss of the female patient, based on a summation of the blood lost during labor operation procedures (indicated by the weight of the blood holding bag) and postnatal operation procedures (indicated by the weight of the blood transfusion bag), and displays the total amount of blood lost by the female patient, on the Liquid Crystal Display monitor, rendered visually accessible to the clinical staff and caretakes in charge of well-being of the female patient. Essentially, the microcontroller also triggers, on the Liquid Crystal Display monitor, a display of the amount of blood lost by the female patient during labor operation procedures (i.e., the weight of the blood holding bag) and the amount of blood lost by the female patient during postnatal operation procedures ((i.e., the weight of the blood holding bag), along with the total quantity of blood lost by the female patient during both labor and postnatal operation/care procedures (sum total of the weight of the blood holding bag and the blood transfusion bag). Further, in the event of the total blood loss (of the female patient) exceeding a predetermined threshold value, the microcontroller also triggers either the sound-based alarm or the light-based alarm or both, and thereby notifies and alerts the clinical staff and the caretakers about the occurrence of excessive blood loss/postpartum hemorrhage in the female patient.

DETAILED DESCRIPTION

In order to overcome the disadvantages of the prior art discussed in the 'background' section and to ensure clinic safety of new-borns and mothers alike, and to promote effective clinical risk management, the present disclosure envisages an effective alternative for commonly used fluid and blood draw sheets, with the alternative solution not only being hygienic, clinically safe in comparison to the prior-art fluid and blood draw sheets but also enabling clinical and hospital staff to make an accurate assessment of the blood lost by a patient, ostensibly a female patient, during labor and postnatal operation procedures.

Figure 1:
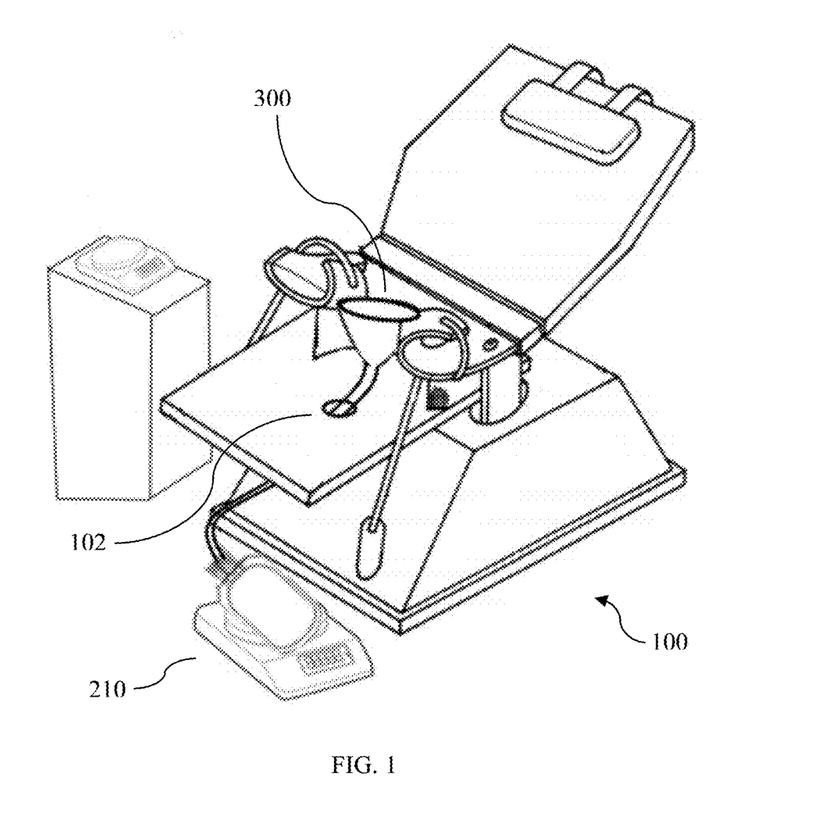
FIG. 1 is a system-level diagram illustrating the apparatus for ascertaining the quantum of blood loss in a female patient undergoing labor and postnatal operation procedures and automatically generating audible alerts indicative of excessive blood loss, in accordance with the present disclosure.

Referring to FIG. 1 of the accompanying drawings, there is shown a typical Labor Delivery Recovery (LDR) bed 100 used for accommodating female patients during labor operation procedures. In accordance with the present disclosure, the LDR bed 100 is used to accommodate a female patient only during labor-related operation procedures, and the (female) patient is transferred onto a different bed, essentially a type-9 bed, post culmination of labor-related operation procedures and at the onset of postnatal operation procedures. While the present disclosure manifests the features of the proposed apparatus, using the LDR bed 100 and type-9 bed (300 in FIG. 3) as examples, those skilled in the art would readily understand that any type of hospital bed could be customized to accommodate the apparatus proposed by the present disclosure. And therefore, the use of LDR Bed 100 and type-9 bed 300 should never be construed in a limiting sense but always in an exemplary sense. And the explanation provided in the present disclosure is never intended to restrict the implementation of the proposed apparatus to LDR bed 100 and type-9 bed 300.

Referring again to FIG. 1, the LDR bed 100 shown therein includes an opening 102 close to the area of the LDR bed where the female patient is likely to rest her pelvis. The opening 102 is large enough to accommodate a substantially cone-shaped proximal end of a first connector 300 (illustrated in more detail in FIG. 3), which is described in elaborate detail in the below paragraphs. The LDR bed 100, in accordance with one embodiment of the present disclosure, is specifically reconfigured to accommodate the apparatus proposed by the present disclosure. Essentially, the LDR bed 100 includes a plurality of hooks (not shown) mounted on the underside (anterior side) of the opening 102, such that the hooks could be used for removably attaching the substantially cone-shaped proximal end of a first connector.

Figure 2:
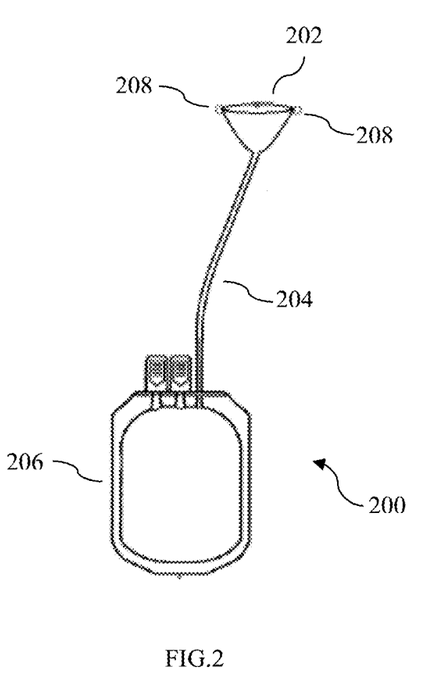
FIG. 2 is a diagram illustrating the construction of the first connector, in accordance with the present disclosure.

Referring to FIG. 2, there is shown a first connector 200, forming a critical part of the apparatus 1000 envisaged by the present disclosure. The first connector 200 includes a substantially coned shaped proximal end denoted by reference numeral 202. The first connector 200 also includes an elongated distal end 204, which is connected to the coned shaped proximal end 202 to form a hose type structure. Preferably, the elongated distal end 204 of the first connector 200 is connected to a blood holding bag 206. And the blood holding bag 206 is disposable and rendered suitable only for single use (one time use). The inner surface of the blood holding bag 206 is coated with an anticoagulant such as sodium citrate to prevent coagulation of the blood collected within the bag 206. Preferably, the blood holding bag 206 is located in proximity to the LDR bed 100, and at a predetermined distance from the LDR bed 100 as permitted by the length of the elongated distal end 204 of the connector 200.

In accordance with the present disclosure, the first connector 200 and especially the (substantially) cone-shaped proximal end 202 of the first connector 200 is removably attached to the area of the LDR bed 100 where the (heavily pregnant) female patient typically rests her pelvis during any labor-related operating procedures. The cone-shaped proximal end 202 of the first connector 200 is secured onto the LDR bed 100, preferably onto the anterior side of the LDR bed 100, directly in-line with the opening 102 of the LDR bed 100, using the hooks 104 mounted on the (underside) of the opening 102. Further, the first connector 200 includes a plurality of rings 208, which when received by the hooks 104, facilitate attachment of the first connector to the LDR bed 100—in an area of the LDR bed 100 likely to receive the pelvic region of the heavily pregnant female patient, especially the posterior pelvic region of the heavily pregnant female patient—through the opening 102, and in turn, attachment of the first connector 200 and essentially the cone-shaped proximal end 202 of the connector 200 to the posterior pelvic region of the female patient, through the opening 102. Essentially, the elongated distal end 204 of the first connector 200 passes through the opening 102 and connects to the blood holding bag 206.

In accordance with the present disclosure, during labor-related operation procedures, the heavily pregnant female patient is made to lie down on the LDR Bed 100 such that the patient's pelvic region, more specifically the posterior pelvic region, rests directly inline and essentially atop the opening 102 of the LDR bed 100. Subsequently, the hooks 104 located essentially on the anterior side of the opening 102 are made to receive respective rings 208 located on the cone-shaped proximal end 202 of the first connector 200 such that the cone-shaped proximal end 202 is (removably) connected to the posterior pelvic region of the female patient accommodated on the LDR bed 100. Essentially, the first connector, and specifically the cone-shaped proximal end 202 of the first connector 200 is secured onto the posterior pelvic region of the female patient and the LDR bed 100 via an operative coupling of the hooks 104 mounted on the anterior side of the opening 102 and the rings 208 present on the cone-shaped proximal end 202 of the first connector 200. In an exemplary embodiment of the present disclosure, the first connector 200 is a standard Type-A connector. And when the heavily pregnant female patient accommodated on the LDR bed 100 starts discharging blood from the posterior pelvic region, the first connector 200, and especially the cone-shaped proximal end 202 of the first connector 200 receives the discharged blood and provides for transfusion of the discharged blood, through the elongated distal end 204 and onto the blood holding bag 206 located in proximity to the LDR bed 100.

In accordance with the present disclosure, the blood holding bag is placed on a first weight sensor 210, such that the first weight sensor 210 measures on a continuous basis the amount of blood transfused into the blood holding 206, and consequentially the amount of blood lost by the heavily pregnant female patient during labor-related operating procedures. Essentially, the first weight sensor (referenced by 210 in FIG. 1) is electronically coupled to a processor, which, in turn, has been configured to detect excessive haemorrhage (bleeding) in pregnant women during labor and postnatal operation procedures, based on the amount of blood lost by pregnant women, and to accordingly issue (audible) sound-based alarms and (visual) light-based alarms indicative of excessive haemorrhage, to clinical staff and caretakers. Preferably, the first weight sensor 210 includes a Radio Frequency Transceiver (not shown in figures) which transmits a first value indicative of the weight of the blood holding bag and consequentially the amount of blood lost by the female patient during the labor operation procedure, to a Radio Frequency Receiver (RF-Receiver; not shown in figures) integrated into the processor.

And, in accordance with the present disclosure, the processor is pre-programmed to continually measure the weight of the blood holding bag (during labor-related operation procedures) and consequently the amount of blood transfused from the body of a (heavily pregnant) female patient, and consequently the blood lost by the female patient during the said labor-related operation procedures. In accordance with the present disclosure, the blood discharged from the female patient's body during labor-related operation procedures is transfused onto the blood holding bag 206. And the first weight sensor 210 continually measures the weight of the blood holding bag 206, thereby providing the processor with an accurate and up-to-date measurement of the amount of blood lost by the female patient during the labor-related operation procedure.

Figure 3:
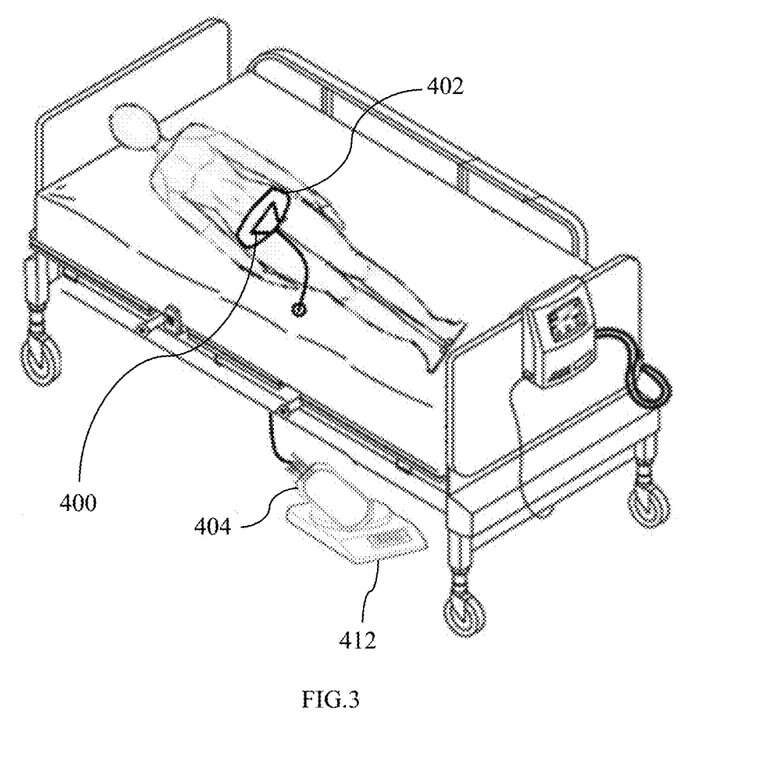
FIG. 3 is a diagram illustrating a specially customized Type-9 bed, in accordance with the present disclosure.

In accordance with the present disclosure, at the culmination of the labor operation procedures, and post successful childbirth as a result of labor operation procedures, the female patient is preferably transferred from the LDR bed 100 to a type-9 bed 300 shown in FIG. 3. Essentially, when the female patient is transferred from the LDR bed 100 to a type-9 bed 300, and also from a labor-related operation procedure to prenatal care, it is imperative that the blood loss from the female patient's body is continually monitored up to a predetermined time period, to entirely rule out the occurrence of complications corresponding to post-partum hemorrhage, to ensure clinic safety of the female patient, and to also comply with standard clinic risk management procedures. Post-partum or postnatal blood loss monitoring assumes an importance equivalent to mentoring of blood loss during labor stage, given that every pregnant female patient is likely to lose at least 500 millilitres of blood up until a day after the childbirth, all the while exhibiting low blood volume, increased heart rate, faintness, and low blood pressure inter-alia, each of which by themselves are serious health ailments. And therefore, it is absolutely necessary that the amount of blood lost by the female patient is monitored even after the culmination of labor operation procedures and during the postnatal stage. And in view of the complication associated with post-natal care, the present disclosure envisages continually monitoring the hemorrhage levels of the female patient even during postnatal care.

In accordance with the present disclosure, soon after the female patient is discharged from labor operation procedure, she is preferably transferred from the LDR bed 100 to a type-9 bed 300. Those reasonably skilled in the art would readily understand that type-9 bed is used only in an exemplary sense and not in a limiting sense and that the apparatus envisaged by the present disclosure can be accommodated and implemented on any other type of hospital bed in an equally effective and efficient manner.

In accordance with the present disclosure, prior to the transfer of the female patient from the LDR bed 100 to the type-9 bed 300, the first connector 200 and essentially the cone-shaped proximal end 202 of the first connector 200 is removed, and the current weight of the blood holding bag 206 is measured by the first weight sensor 210 and electronically transmitted to the processor. Subsequently, when the female patient is transferred from the LDR bed 100 to the type-9 bed 300, a second connector is used to monitor the blood hemorrhage (during the postnatal stage) from the body of the female patient.

Figure 4A:
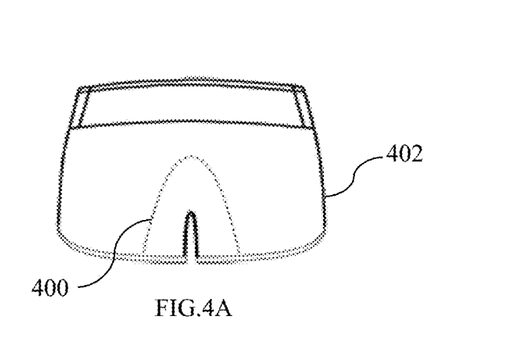
FIGS. 4A-4C illustrate respectively the front view, back view, and top view of the second connector woven onto an undergarment to be worn by a female patient undergoing postnatal operation procedures.

In accordance with a preferred embodiment of the present disclosure, during postnatal care or postnatal operation procedures, the female patient is made to wear a specially stitched undergarment, the specially stitched undergarment integrated with a second connector 400, essentially a type-B connector, for measuring the quantum of blood lost by the female patient during postnatal/post-partum operation procedures. The second connector 400 essentially includes a substantially rectangular-shaped proximal end, and an elongated hose shaped distal end. Essentially, the substantially rectangular proximal end is woven onto an undergarment to be worn by the female patient, while the distal end is connected to a blood transfusion bag located in proximity to the type-9 bed 300.

Figure 4B:
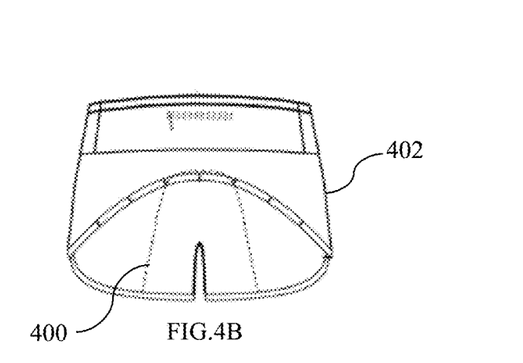
Figure 4C:
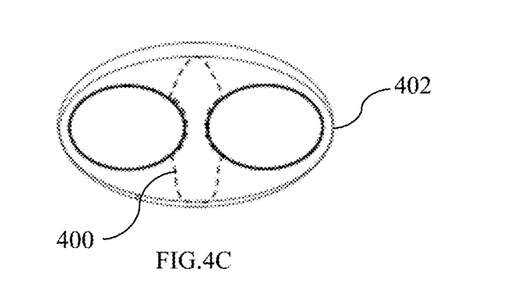
Figure 4D:
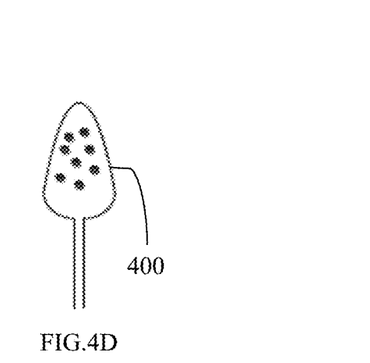
FIGS. 4D-4E respectively illustrate the front view and the back view of the second connector, in accordance with the present disclosure.
Figure 4E:
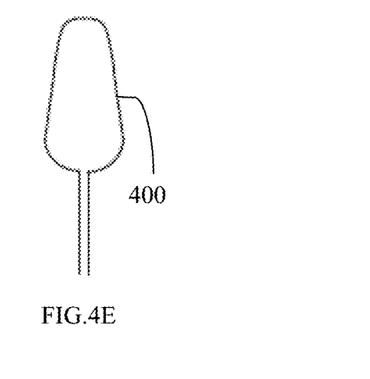

In accordance with the present disclosure, the second connector 400 is woven onto the undergarment 402 to be worn by the female patient while undergoing postnatal/postpartum care. FIG. 4A-4C of the accompanying drawings respectively illustrate the front view, back view, and top view of the second connector 400 woven onto the undergarment 402 (to be) worn the female patient while undergoing postnatal operation procedures or postnatal care. Further, FIG. 4D-4E illustrate the front view and the back view of the second connector 400. In accordance with the present disclosure, soon after the female patient wears the specially designed undergarment 402 woven with the second connector 400, the second connector 400 facilitates absorption of blood from the female patient's body via the use of predetermined sterile gases and sanitary absorbents. Essentially, the second connector 400 is woven onto the undergarment 402 in such a way that the second connector 400 gets in contact with the posterior pelvic region of the female patient. Subsequently, the distal end of the second connector 400, which resembles an elongated hose in terms of the construction, is attached to a second blood transfusion bag 404. Preferably, the type-9 bed accommodating the female patient (during postnatal operation procedures) includes a hole of predetermined size created in the middle portion (both laterally and longitudinally) of the bed body (of the type-9 bed) such that the distal end of the second connector 400 passes through the hole and connects to the second blood transfusion bag 404.

In accordance with the present disclosure, the second connector 400 facilitates absorption of blood from the female patient's body via the use of sterile gases and sanitary absorbents. And the blood absorbed via the use of sterile gases and sanitary absorbents is transfused via the distal end of the second connector 400 and onto the second blood transfusion bag 404. The blood transfusion bag 404 is placed on a second weight sensor 412, such that the second weight sensor 412 measures on a continuous basis the amount of blood absorbed from the female patient's body through sterile gases and sanitary absorbents and transfused onto the second blood transfusion bag. Consequently, the second weight sensor 412 measures the amount of blood lost by the female patient during postnatal care or postnatal operation procedures, for the amount of blood lost by the female patient through sterile gases and sanitary absorbents is equivalent to the amount of blood transfused into the second blood transfusion bag 404. Typically, the second weight sensor 412 is also electronically coupled to the processor, which in turn, also receives information corresponding to the amount of blood lost by the female patient during labor operation procedures via the first weight sensor 210. Preferably, the second weight sensor 412 includes a Radio Frequency Transceiver (not shown in figures) which transmits a second value indicative of the weight of the blood transfusion bag and consequentially the amount of blood lost by the female patient during the postnatal operation procedure, to a Radio Frequency Receiver (RF-Receiver; not shown in figures) integrated into the processor.

The processor, in accordance with the present disclosure, is connected to the first weight sensor 210, the second weight sensor 412, and a Liquid Crystal Display (LCD) monitor (not shown in figures) which, in turn, is configured to display the amount of blood lost by the female patient during the labor operation procedures and postnatal operation procedure. The processor, in accordance with the present disclosure is a microcontroller forming a part of an electronic circuitry configured to communicably couple said microcontroller with the first weight sensor 210, the second weight sensor 412, the LCD, and at least one sound-based alarm (not shown in figures), and at least one light-based alarm (not shown in figures).

The processor, which, in accordance with the present disclosure, communicates with the first weight sensor 210 and the second weight sensor 412 via Radio Frequency (RF), and with a frequency band of 2.4 GHz, receives the weight of the blood holding bag 206 from the first weight sensor 210. Subsequently, the processor receives the weight of the second blood transfusion bag 404 from the second weight sensor 412. Subsequently, based on the weight of the first blood holding bag 206 received from the first weight sensor 210, the processor determines the amount of blood lost by the female patient during the labor operation procedures and while accommodated on the LDR bed 100. Similarly, based on the weight of the second blood transfusion bag 404 received from the second weight sensor 412, the processor determines the amount of blood absorbed from the body of the female patient by the use sterile gases and sanitary absorbents during postnatal care/operation procedures. Subsequently, the processor calculates a summation of the blood lost by the female patient during the labor operation procedure and the postnatal care/operation procedure and generates a numerical value indicative of the total amount of blood lost by the female patient (during the combination of labor operation procedures and postnatal operation procedures).

In accordance with the present disclosure, the electronic circuitry incorporating the processor also includes (at least one) sound-based alarm and light-based alarm, which in turn, are triggered by the processor in an event the value indicative of the total blood lost by the female patient (i.e., summation of the blood lost by the female patient during the labor operation procedure and the postnatal care/operation procedure) exceeds a predetermined threshold value. In accordance with an exemplary embodiment, the Liquid Crystal Display is arranged such that it is readily accessible to the clinic staff in charge of the well-being of the female patient. Likewise, the sound-based alarm and light-based alarm are also located such that they are easily visible and audible to the clinical staff in charge of the well-being of the said female patient. Further, it is also possible that when the value indicative of the total blood lost by the female patient exceeds the predetermined threshold value, the microcontroller triggers the sound-based alarm followed by the light-based alarm. However, it is also possible the order of triggering of the sound-based alarm and the light-based alarm is reversed or that both the alarms are simultaneously triggered.

In accordance with the present disclosure, the processor is configured to store a first value indicative of the amount of blood lost by the female patient during the labor operation procedures, a second value indicative of the amount of blood absorbed from the body of the female patient by the use sterile gases and sanitary absorbents during postnatal care/operation procedures, and a third value indicative of the total blood lost by the female patient during the combination of labor operation procedures and postnatal operation procedures, in either a computer-readable repository or a computer-readable memory card, such that the first value, second value, and the third value are readily accessed by the clinical staff via a suitably programmed computer for an immediate analysis of the current health condition of the female patient.

Figure 5A:
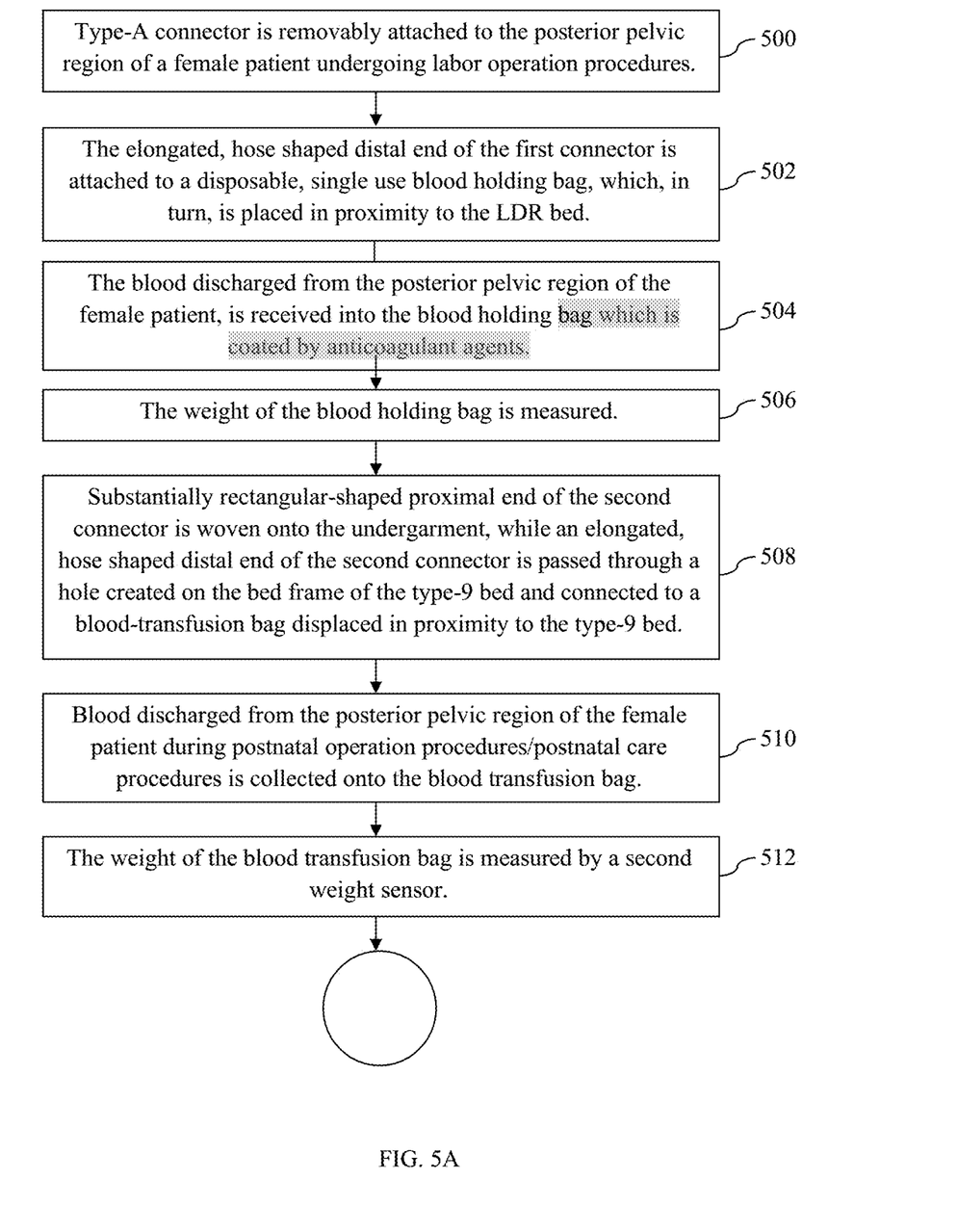
FIGS. 5A and 5B in combination illustrate a flowchart describing the steps involved in a method for detecting and quantifying blood loss in a female patient during labor and postnatal procedures, and generating audible alerts in an event excessive blood loss in witnessed in the female patient, in accordance with the present disclosure.
Figure 5B:
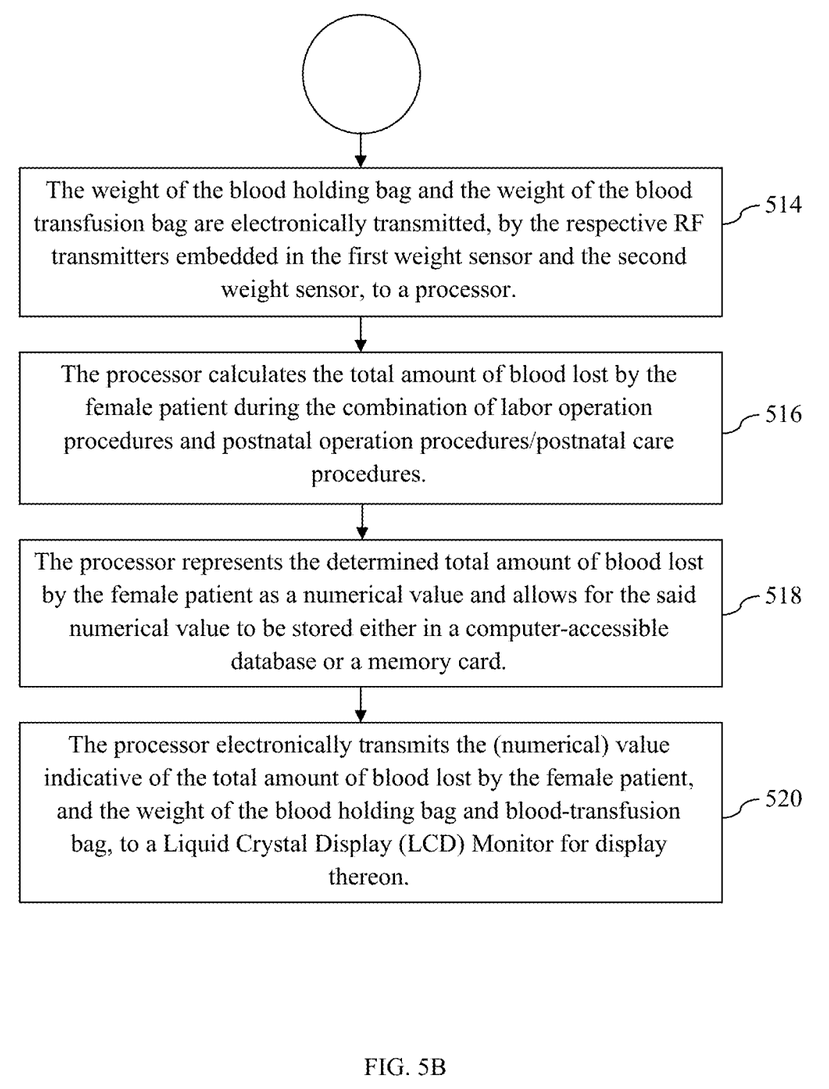

Referring to FIG. 5A and FIG. 5B in combination, there is shown a flowchart illustrating the steps involved in a method for detecting and quantifying blood loss in a female patient during labor and postnatal procedures, and generating audible alerts in an event excessive blood loss in witnessed in the female patient during either labor operation procedures or postnatal (post-partum) operation procedures or both. The method, as illustrated in the flowchart, begins at step 500, at which a first connector, essentially a type-A connector, is removably attached to the posterior pelvic region of a female patient undergoing labor operation procedures. The first connector includes a substantially cone-shaped proximal end and an elongated, hose shaped distal end. The (substantially cone-shaped) proximal end is attached to the posterior pelvic region of the female patient when the female patient is resting upon a customized Labor Delivery Recovery (LDR) bed. The LDR bed is customized in the sense that it includes an opening located essentially on the anterior side thereof through which the proximal end of the first connector could be inserted and made to establish a skin-contact with the posterior pelvic region of the female patient. Subsequently, at step 502, the elongated, hose shaped distal end of the first connector is attached to a disposable, single use blood holding bag, which, in turn, is placed in proximity to the LDR bed. Essentially, the proximity between the LDR bed and the blood holding bag is directly proportional to the length of the elongated, hose shaped distal end; i.e., greater the length of the elongated, hose shaped distal end, greater could be the distance between the LDR bed and the blood holding bag.

In accordance with the present disclosure, at step 504, the blood discharged from the body, i.e., the posterior pelvic region of the female patient, is received into the blood holding bag which inner surface has been coated with an anticoagulant such as Sodium Citrate in order to prevent coagulation of the collected blood. Essentially, the blood discharged from the female patient's body is directed from the proximal end and the distal end through to the blood holding bag. After the blood is received onto the blood holding bag, the weight of the blood holding bag is measured at step 506. Essentially, a weight sensor having an integrated Radio Frequency Transceiver is utilized for the purpose of measuring the weight of the blood holding bag. Essentially, the (current) weight of the blood holding bag reveals the amount of blood lost by the female patient and therefore, the amount of blood present within the blood holding bag is presumed to be equivalent to the amount of blood lost by the female patient during the labor operation procedures.

Soon after the labor operation procedures are ended, implementation of step 508 is initiated. Essentially, at step 508, soon after the culmination of the labor operation procedures, postnatal operation procedures or postnatal care procedures are initiated, and the female patient is transferred from the LDR bed which was customized for labor operation procedures to a type-9 bed which is customized for postnatal operation procedures/postnatal care procedures. With the transferal of the female patient from the LDR bed to the type-9 bed, the first connector, which was in skin-contact with the posterior pelvic region of the female patient, is removed. And subsequently the female patient is instructed to wear an undergarment, which includes a second connector woven into it. The second connector, essentially a type-B connector, is woven onto the undergarment in such a way that the second connector establishes skin-contact with the posterior pelvic region of the female patient, all the while extending both laterally and longitudinally from the posterior pelvic region of the female patient to the anterior pelvic region of the female patient. Essentially, at step 508, a substantially rectangular-shaped proximal end of the second connector is woven onto the undergarment, while an elongated, hose shaped distal end of the second connector is passed through a hole created on the bed frame of the type-9 bed and connected to a blood-transfusion bag displaced in proximity to the type-9 bed. Essentially, the proximity between the type-9 bed and the blood-transfusion bag is directly proportional to the length of the elongated distal end of the second connector, as was the case with the LDR bed and the distal end of the first connector.

Further, at step 510, with the substantially rectangular-shaped proximal end of the second connector being woven onto the undergarment and the undergarment worn by the female patient, and the elongated, hose shaped distal end of the second connector being passed through the hole created on the bed frame of the type-9 bed and connected to the blood transfusion bag, the blood discharged from the female patient's body, i.e., from the posterior pelvic region of the female patient during postnatal operation procedures/postnatal care procedures is collected onto the blood transfusion bag. Essentially, during postnatal operation procedures or postnatal care procedures, blood is absorbed from the female patient's posterior pelvic region through the use of sterile gases and sanitary absorbents. In accordance with the present disclosure, the second connector facilitates absorption of blood from the female patient's body via predetermined sterile gases and sanitary absorbents. And, therefore, at step 510, a certain quantum of blood is absorbed from the female patient's body via the predetermined sterile gases and sanitary absorbents. And the blood thus absorbed is transfused into the blood-transfusion bag, flowing through the proximal end and distal end of the second connector, finally to the blood-transfusion bag.

Subsequently, at step 512, the weight of the blood transfusion bag is measured by a second weight sensor, also equipped with a Radio Frequency Transceiver (RF-Transceiver). As was the case with the first weight sensor and the blood holding bag, the weight of the blood-transfusion bag dictates the amount of blood lost by the female patient during the postnatal operation procedures/postnatal care procedures. Further, at step 514, the weight of the blood holding bag—measured by the first weight sensor, and the weight of the blood transfusion bag—measured by the second weight sensor, are electronically transmitted, by the respective RF transmitters embedded in the first weight sensor and the second weight sensor, to a processor, preferably a microcontroller having an integrated Radio Frequency Receiver (RF-Receiver). Further, at step 516, the processor, after receiving the weight of the blood holding bag and the weight of the blood transfusion bag (from the first weight sensor and the second weight sensor respectively), calculates the total amount of blood lost by the female patient during the combination of labor operation procedures and postnatal operation procedures/postnatal care procedures. Essentially, the processor summates the weights of the blood holding bag and blood-transfusion bag and determines the total amount of blood lost by the female patient. Further, at step 518, the processor represents the thus determined total amount of blood lost by the female patient as a numerical value and allows for the said numerical value to be stored either in a computer-accessible database or a memory card. Further, at step 520, the processor, which, in turn, is a microcontroller, electronically transmits the (numerical) value indicative of the total amount of blood lost by the female patient, and the weight of the blood holding bag and blood-transfusion bag, to a Liquid Crystal Display (LCD) Monitor, which, in turn, displays the total amount of blood lost by the female patient and the bold lost by the female patient during labor operation procedures (equivalent to the weight of the blood holding bag), and the blood lost by the bold lost by the female patient during postnatal operation procedures/postnatal care procedures (equivalent to the weight of the blood-transfusion bag), for the said blood measurements to be viewed and analyzed by a clinical team in charge of the well-being of the female patient. Additionally, the processor triggers at least one of a sound-based alarm and light-based alarm, or alternatively triggers both the sound-based alarm and the light-based alarm both, in an event the total amount of blood lost by the female patient is determined to be exceeding a predetermined threshold value. Essentially, the sound-based alarm and the light-based alarm are interconnected with the processor via an electronic circuitry that enables the processor to selectively trigger the sound-based alarm and the light-based alarm, both simultaneously and individually.

TECHNICAL ADVANTAGES

The technical advantages envisaged by the present disclosure include the realization of an electronic system (apparatus) that facilitates automated and continued monitoring of the amount of blood lost by a female patient during both labor operation procedures and postnatal operation procedures. The system (envisaged by the present disclosure) obviates the need for manual inspection of the amount of blood lost by a female patient, and instead relies upon a plurality of weight sensors to accurately measure the quantum of blood loss during labor and postnatal operation procedures. The accuracy in the measurement of blood lost translates into an accurate prediction of the onset of postpartum haemorrhage, for any measurement errors associated with visual inspection of blood loss is obviated. Further, the system also obviates the necessity for manual intervention in terms of detecting and identifying postpartum haemorrhage, for the system envisages an electronic circuitry embedded with a microcontroller configured to accurately process the information provided by the weight sensors, and thus arrive at an accurate measurement of the total amount of blood lost by the female patient during labor and postnatal operation procedures, and consequentially trigger, automatically and without necessitating manual intervention, a sound-based alarm as well as a light-based alarm, in an event the blood loss attributed to the female patient is determined—by the microcontroller—to exceed a predetermined threshold value.

What is claimed is:

1. An apparatus for use in labor and postnatal operation procedures, said apparatus configured to generate audible alerts in an event of excessive blood loss in a female patient during said labor and postnatal operation procedures, said apparatus comprising:

a first connector having a cone-shaped proximal end and an elongated distal end, said cone-shaped proximal end in skin-contact with a posterior pelvic region of said female patient only during said labor operation procedures, through an opening created in an Labor Recovery Delivery bed accommodating said female patient, said elongated distal end connected to a blood holding bag located in proximity to said Labor Recovery Delivery bed, said blood holding bag receiving blood discharged from said female patient during said labor operation procedures, through said proximal end and said elongated distal end of said first connector, and wherein at least an inner surface of said blood holding bag is coated with an anticoagulant;

a first weight sensor configured to measure a weight of said blood holding bag in terms of an amount of blood collected therein;

a second connector removably connected to said posterior pelvic region of said female patient, during only said postnatal operation procedures, wherein said second connector is woven onto an undergarment to be worn by said female patient during said postnatal operation procedures such that said second connector is in skin-contact with said posterior pelvic region of said female patient, said second connector facilitating transfusion of blood from said female patient's body through predetermined sanitary absorbents and sterile medical gases, onto a blood-transfusion bag located in proximity to a type-9 bed accommodating said female patient during said postnatal operation procedures;

a second weight sensor configured to measure a weight of said blood-transfusion bag in terms of an amount of blood transfused thereto;

a processor forming at least a part of a processing circuitry configured to detect and quantify blood loss in said female patient during said labor and postnatal operation procedures, said processor configured to electronically receive said weight of said blood holding bag and said weight of said blood-transfusion bag, from said first weight sensor and said second sensor respectively, said processor configured to calculate total amount of blood lost by said female patient, based on said weight of said blood holding bag and said weight of said blood-transfusion bag, said processor further configured to:

store a numerical value indicative of said total amount of blood lost by said female patient, as an entry, in a database;

selectively trigger at least one predetermined light-based alarm and sound-based alarm embedded onto said processing circuitry, in an event said numerical value indicative of said total amount of blood lost by said female patient exceeds a predetermined threshold value.

2. The apparatus as claimed in claim 1, wherein said opening of said Labor Recovery Delivery bed includes a plurality of hooks displaced on an anterior periphery thereof, each of said plurality of hooks receiving respective rings displaced on said cone-shaped proximal end of said first connector, such that said cone-shaped proximal end of said first connector is removably attached to said anterior side of said Labor Recovery Delivery bed and to said posterior pelvic region of said female patient, via said opening.

3. The apparatus as claimed in claim 1, wherein said first connector is in skin-contact with said posterior pelvic region of said female patient only during said labor operation procedures, and wherein said second connector is in skin-contact with said posterior pelvic region of said female patient only during said postnatal operation procedures.

4. The apparatus as claimed in claim 1, wherein said first connector in skin-contact with said posterior pelvic region of said female patient during said labor operation procedures, is replaced by said second connector during said postnatal operation procedures.

5. The apparatus as claimed in claim 1, wherein said second connector is a type-B connector, and wherein said second connector is woven onto said undergarment, said second connector extending from a posterior side of said undergarment to an anterior side thereof, such that said second connector extends laterally and longitudinally from said posterior pelvic region of said female patient to an anterior pelvic region of said female patient.

6. The apparatus as claimed in claim 5, wherein said second connector includes a plurality of perforations etched thereupon, to facilitate airflow into said undergarment worn by said female patient, and prevent sweating of said posterior pelvic region of said female patient.

7. The apparatus as claimed in claim 5, wherein said second connector includes at least two longitudinal edges and at least two lateral sides, and wherein said longitudinal edges and lateral sides are curved to a predetermined degree, in order to prevent leakage of blood therefrom.

8. The apparatus as claimed in claim 1, wherein a substantially rectangular proximal end of said second connector is woven onto said undergarment to be worn by said female patient, and wherein an elongated distal end of second connector is connected to said blood-transfusion bag via a hole created on a bed-frame of said type-9 bed.

* * * * *